(12) United States Patent
Pan et al.

(10) Patent No.: US 12,162,812 B2
(45) Date of Patent: Dec. 10, 2024

(54) PRECURSOR COMPOUND OF TETRACYCLIC HYDROCARBON AND PREPARATION METHOD THEREOF, AND TETRACYCLIC HYDROCARBON AND PREPARATION METHOD AND USE THEREOF

(71) Applicant: TIANJIN UNIVERSITY, Tianjin (CN)

(72) Inventors: Lun Pan, Tianjin (CN); Jijun Zou, Tianjin (CN); Xinfang Zhang, Tianjin (CN); Chengxiang Shi, Tianjin (CN); Li Wang, Tianjin (CN); Xiangwen Zhang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 18/621,888

(22) Filed: Mar. 29, 2024

(65) Prior Publication Data

US 2024/0327318 A1 Oct. 3, 2024

(30) Foreign Application Priority Data

Mar. 31, 2023 (CN) .......................... 202310332974.9

(51) Int. Cl.
*C07C 13/68* (2006.01)
*C07C 1/207* (2006.01)
(Continued)

(52) U.S. Cl.
CPC ............ *C07C 13/68* (2013.01); *C07C 1/2076* (2013.01); *C07C 45/45* (2013.01); *C07C 49/423* (2013.01); *C07C 2603/86* (2017.05)

(58) Field of Classification Search
None
See application file for complete search history.

(56) References Cited

U.S. PATENT DOCUMENTS 4,203,930 A 5/1980 Myers, Jr.

FOREIGN PATENT DOCUMENTS

CN 108865260 A 11/2018
CN 110511794 A 11/2019
(Continued)

OTHER PUBLICATIONS

Gao "JP-10 combustion studied with shock tube experiments and modeled with automatic reaction mechanism generation," Combustion and Flame 162(8): 3115-3129 (2015).

*Primary Examiner* — In Suk C Bullock
*Assistant Examiner* — Alyssa L Cepluch
(74) *Attorney, Agent, or Firm* — MEDLER FERRO WOODHOUSE & MILLS PLLC

(57) ABSTRACT

Provided are a precursor compound of a tetracyclic hydrocarbon and a preparation method thereof, and a tetracyclic hydrocarbon and a preparation method and use thereof. The precursor compound of the tetracyclic hydrocarbon with a structure shown in formula I has a polycyclic structure. The precursor compound is subjected to hydrodeoxygenation so as to be prepared into the tetracyclic hydrocarbon with a structure shown in formula II that has a high density (0.986 g/cm$^3$), a high calorific value (41.14 MJ/L), and a low freezing point (less than −60° C.).

formula I (Continued)

-continued

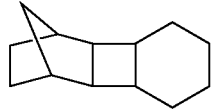

formula II

7 Claims, 2 Drawing Sheets

(51) Int. Cl.
*C07C 45/45* (2006.01)
*C07C 49/423* (2006.01)

(56) References Cited

FOREIGN PATENT DOCUMENTS

| | | | |
|---|---|---|---|
| CN | 111233615 | A | 6/2020 |
| CN | 115215819 | A | 10/2022 |
| CN | 115259991 | A | 11/2022 |

PRECURSOR COMPOUND OF TETRACYCLIC HYDROCARBON AND PREPARATION METHOD THEREOF, AND TETRACYCLIC HYDROCARBON AND PREPARATION METHOD AND USE THEREOF

CROSS REFERENCE TO RELATED APPLICATION

This patent application claims the benefit and priority of Chinese Patent Application No. 202310332974.9 filed with the China National Intellectual Property Administration on Mar. 31, 2023, the disclosure of which is incorporated by reference herein in its entirety as part of the present application.

TECHNICAL FIELD

The present disclosure relates to the technical field of fuels, and specifically to a precursor compound of a tetracyclic hydrocarbon and a preparation method thereof, and a tetracyclic hydrocarbon and a preparation method and use thereof.

BACKGROUND

High-energy-density hydrocarbon fuels are widely used in aerospace vehicles such as missiles and aircraft. The propulsion performance of an engine depends to a large extent on the characteristics of the fuel used, among which the density and volumetric net heat of combustion (NHOC) have a crucial impact on the propulsion performance of the aircraft. In addition, considering a low-temperature environment in which the aircraft operates, it is needed for high-density hydrocarbon fuels to have both low freezing point and low viscosity to ensure normal transportation. Therefore, it is an effective way to improve the overall performance of the aircraft at low cost by increasing the energy density of fuel while reducing the freezing point of fuel.

The high-density hydrocarbon fuels (with densities greater than 0.85 g/cm³) are generally alkane fuels (such as RJ-4, RJ-4-1, and JP-10) prepared by alkylation and hydroisomerization. Studies have found that the density and calorific value of polycycloalkane hydrocarbon fuels increase with an increase of the carbon number and ring number, but the volumetric NHOC decreases with an increase of the carbon/hydrogen (C/H) ratio. Accordingly, it is of great significance to synthesize fuels with a high density and a high calorific value as well as desirable low-temperature performances.

SUMMARY

In view of this, the present disclosure is to provide a precursor compound of a tetracyclic hydrocarbon and a preparation method thereof, and a tetracyclic hydrocarbon and a preparation method and use thereof. In the present disclosure, the precursor compound of the tetracyclic hydrocarbon has a polycyclic structure, and the precursor compound could be used to prepare a tetracyclic hydrocarbon fuel with a high density and a high calorific value as well as low freezing point.

To achieve the above object, the present disclosure provides the following technical solutions:

Provided is a precursor compound of a tetracyclic hydrocarbon, the precursor compound having a structure shown in formula I:

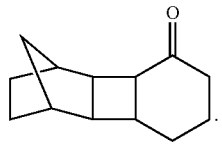

formula I

Also provided is a method for preparing the precursor compound of the tetracyclic hydrocarbon, including the following steps:

subjecting norbornene and cyclohexenone to photosensitized cycloaddition under ultraviolet (UV) irradiation to obtain the precursor compound of the tetracyclic hydrocarbon.

In some embodiments, a molar ratio of the norbornene to the cyclohexenone is in a range of 1:4 to 4:1.

In some embodiments, the photosensitized cycloaddition is conducted in an organic solvent, and the organic solvent includes at least one selected from the group consisting of an alcohol solvent, a chlorinated alkane solvent, and a cycloalkane solvent.

In some embodiments, the photosensitized cycloaddition is conducted at a temperature of −10° C. to 30° C. for 1 h to 9 h; and the UV irradiation has an incident light flux of 50 mW/cm² to 150 mW/cm².

Also provided is a tetracyclic hydrocarbon, the tetracyclic hydrocarbon having a structure shown in formula II:

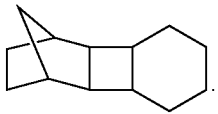

formula II

Also provided is a method for preparing the tetracyclic hydrocarbon, including the following steps:

subjecting a precursor compound of the tetracyclic hydrocarbon to hydrodeoxygenation in a hydrogen atmosphere to obtain the tetracyclic hydrocarbon;

where the precursor compound of the tetracyclic hydrocarbon is the precursor compound of the tetracyclic hydrocarbon described above or the precursor compound of the tetracyclic hydrocarbon prepared by the method described above.

In some embodiments, the hydrodeoxygenation is conducted in the presence of a hydrodeoxygenation catalyst, a molecular sieve, and a solvent;

the hydrodeoxygenation catalyst includes a transition metal catalyst;

the molecular sieve includes at least one selected from the group consisting of an H-Y molecular sieve, a Pt/H-Y molecular sieve, a ZSM-5 molecular sieve, and an H-β molecular sieve;

a mass ratio of the molecular sieve to the hydrodeoxygenation catalyst is in a range of 5:1 to 8:1;

the solvent includes a cycloalkane solvent; and the hydrodeoxygenation is conducted at a temperature of 160° C. to 200° C. and a hydrogen pressure of 0.5 MPa to 6 MPa for 1 h to 12 h.

Also provided is use of the tetracyclic hydrocarbon or the tetracyclic hydrocarbon prepared by the method described above as a fuel.

In some embodiments, the fuel includes an aerospace fuel.

In the present disclosure, the precursor compound of the tetracyclic hydrocarbon with a structure shown in formula I has a polycyclic structure. The precursor compound is subjected to hydrodeoxygenation so as to be prepared into the tetracyclic hydrocarbon with a structure shown in formula II that has a high density, a high calorific value, and a low freezing point.

The present disclosure provides a method for preparing the precursor compound of the tetracyclic hydrocarbon. Cyclohexenone serves as both a self-sensitizer and a reaction substrate and could be prepared into the precursor compound of the tetracyclic hydrocarbon by photosensitized cycloaddition with norbornene. The photosensitized cycloaddition is not sensitive to temperature and could occur at ambient temperature, which has few by-products and high product selectivity. After the photosensitized cycloaddition, unreacted substrates could be easily separated from the product. The separation and purification of the product has low cost, and the product has a high yield and a high purity. The method has low energy consumption, is environmental-friendly, and is suitable for industrial production.

In the present disclosure, the tetracyclic hydrocarbon with a structure shown in formula II has a density of 0.986 g/cm$^3$, a volumetric net calorific value of 41.14 MJ/L, and a freezing point of less than −60° C. The tetracyclic hydrocarbon exhibits a high density, a high volumetric net calorific value, and a low freezing point and excellent combustion and low-temperature resistance properties. When being used as a fuel, the tetracyclic hydrocarbon could exhibit dual functions of ensuring the flexibility and portability of an aircraft and effectively improving the range, speed, payload and other aircraft performances of the aircraft. Therefore, the tetracyclic hydrocarbon has desirable application prospects in the aerospace field.

The present disclosure provides a method for preparing the tetracyclic hydrocarbon, where the tetracyclic hydrocarbon could be prepared by hydrodeoxygenation on the precursor compound of the tetracyclic hydrocarbon. The method has simple reaction process, few by-products, high product selectivity, low cost of product separation and purification, and low energy consumption, and is environmental-friendly, which is suitable for large-scale production.

DETAILED DESCRIPTION OF THE EMBODIMENTS

Figure 1:
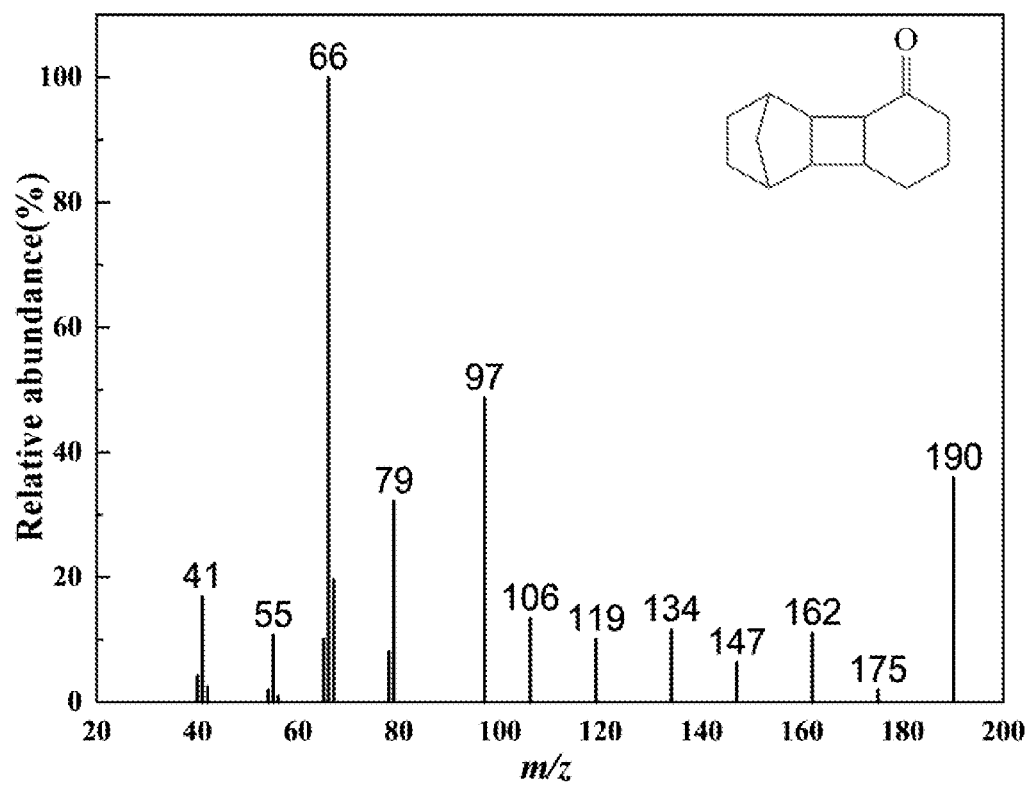
FIG. 1 shows a mass spectrum of the precursor compound of the tetracyclic hydrocarbon prepared in Example 1.

The present disclosure provides a precursor compound of a tetracyclic hydrocarbon, the precursor compound having a structure shown in formula I:

The present disclosure further provides a method for preparing the precursor compound of the tetracyclic hydrocarbon described above, including the following steps:

subjecting norbornene and cyclohexenone to photosensitized cycloaddition under UV irradiation to obtain the precursor compound of the tetracyclic hydrocarbon.

Unless otherwise specified, all raw materials used in the present disclosure are commercially available commodities.

In some embodiments, a molar ratio of the norbornene to the cyclohexenone is in a range of 1:4 to 4:1, preferably 1:3 to 3:1, and more preferably 4:1, 3:1, 2:1, 1:1, 1:2, 1:3, or 1:4. As the amount of the norbornene increases, a conversion rate of the cyclohexenone also gradually increases, while a conversion rate of the norbornene gradually decreases. At the same time, a selectivity of a target product copolymer shows a gradually increasing trend.

In some embodiments, the photosensitized cycloaddition is conducted in an organic solvent, and the organic solvent includes at least one selected from the group consisting of an alcohol solvent, a chlorinated alkane solvent, and a cycloalkane solvent. In some embodiments, the alcohol solvent is a lower alcohol, and preferably ethanol and/or methanol. In some embodiments, the chlorinated alkane solvent includes dichloromethane. In some embodiments, the cycloalkane solvent includes cyclohexane.

In some specific embodiments of the present disclosure, the photosensitized cycloaddition of the norbornene and the cyclohexenone under UV irradiation is performed by: mixing the norbornene, the cyclohexenone, and the organic solvent to obtain a mixture, introducing a protective atmosphere into the mixture, and subjecting the mixture to the photosensitized cycloaddition under UV irradiation. There is no special limitation on the mixing, and a mixing method well known to those skilled in the art that could make the raw materials be mixed evenly may be used, such as stirring and mixing. In some embodiments, the introduction of the protective atmosphere is conducted for 0.5 h to 2 h, and preferably 1 h to 1.5 h. In some embodiments, the protective atmosphere is nitrogen or an inert gas, and the inert gas is helium and/or argon. In the present disclosure, by introducing the protective atmosphere, oxygen could be removed to prevent same from interfering with the reaction.

In some embodiments, the photosensitized cycloaddition is conducted at a temperature of −10° C. to 30° C., preferably 0° C. to 20° C., and more preferably −10° C., 0° C., 10° C., 20° C., or 30° C. In some embodiments, the photosensitized cycloaddition is conducted for 1 h to 9 h, preferably 2 h to 8 h, and more preferably 1 h, 2 h, 3 h, 4 h, 5 h, 6 h, 7 h, 8 h, or 9 h. In some embodiments, the UV irradiation has an incident light flux of (50-150) mW/cm$^2$, and preferably 50 mW/cm$^2$, 100 mW/cm$^2$, or 150 mW/cm$^2$. In some embodiments, the incident light flux is adjusted according to current and voltage. In an embodiment, the UV is provided by a 365 nm LED strip. During the photosensitized cycloaddition, a [2+2] cycloaddition reaction occurs between the norbornene and the cyclohexenone, with a reaction formula as shown in formula 1:

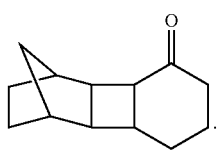

formula I

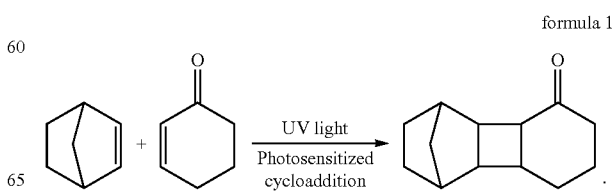

formula 1

In some embodiments, after the photosensitized cycloaddition, a post-treatment is conducted. In some embodiments, the post-treatment includes: concentrating an obtained reaction solution and then purifying by vacuum distillation to obtain the precursor compound of the tetracyclic hydrocarbon. There is no special limitation on the concentration, and any concentration method well known to those skilled in the art may be used, such as rotary evaporation. In some embodiments, the concentration is conducted at a temperature of 40° C. to 60° C., and preferably 45° C. to 55° C. The purpose of the concentration is to remove lower-boiling solvents. In some embodiments, the purification is conducted by vacuum distillation. In some embodiments, the vacuum distillation is conducted at a pressure of 0.04 MPa to 0.1 MPa, and preferably 0.06 MPa to 0.08 MPa. In some embodiments, the vacuum distillation is conducted at a temperature of 150° C. to 220° C., and preferably 160° C. to 200° C. In the present disclosure, the precursor compound with a high boiling point could be obtained by purification by the vacuum distillation.

In the method for preparing the precursor compound of the tetracyclic hydrocarbon provided by the present disclosure, the cyclohexenone acts as a self-sensitizer as well as a reaction substrate to undergo [2+2] cycloaddition with norbornene. After the photosensitized cycloaddition, the unreacted substrate could be easily separated from the product and there are fewer by-products, which is conducive to obtaining the precursor compound of the tetracyclic hydrocarbon with a high density and excellent performance. Moreover, the photosensitized cycloaddition has mild conditions and few by-products, making it suitable for large-scale production and industrial applications. Meanwhile, the self-sensitized [2+2] cycloaddition is not sensitive to temperature and could be done at ambient temperature and normal pressure. When the temperature changes from −10° C. to 30° C., there is almost no change in the conversion rates of the norbornene and the cyclohexenone as well as the selectivity of copolymerization products and autopolymerization products almost. Compared with other homogeneous catalysts (such as non-conjugated ketone-cyclohexanone), in the present disclosure, the cyclohexenone with a conjugated structure is used as a raw material for the photosensitized cycloaddition, resulting in less by-products. The present disclosure provides a tetracyclic hydrocarbon with a structure shown in formula II.

formula II

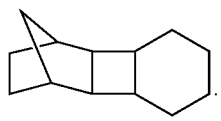

In the present disclosure, the tetracyclic hydrocarbon has a density of 0.986 g/cm³, a volumetric net calorific value of 41.14 MJ/L, and a freezing point of less than −60° C.

The present disclosure further provides a method for preparing the tetracyclic hydrocarbon, including the following steps:
 subjecting a precursor compound of the tetracyclic hydrocarbon to hydrodeoxygenation in a hydrogen atmosphere to obtain the tetracyclic hydrocarbon;
 where the precursor compound of the tetracyclic hydrocarbon is the precursor compound of the tetracyclic hydrocarbon described above or the precursor compound of the tetracyclic hydrocarbon prepared by the method described above.

In some embodiments, the hydrodeoxygenation is conducted in the presence of a hydrodeoxygenation catalyst, a molecular sieve, and a solvent. In some embodiments, the hydrodeoxygenation catalyst includes a transition metal catalyst. In some embodiments, a transition metal in the transition metal catalyst is a Group VIII metal, and preferably, the transition metal catalyst includes at least one of Pt/C, Rh/C, Pd/C, and Pd/TiO₂. In some embodiments, the molecular sieve is at least one selected from the group consisting of an H-Y molecular sieve, a Pt/H-Y molecular sieve, a ZSM-5 molecular sieve, and an H-β molecular sieve. In some embodiments, a mass ratio of the molecular sieve to the hydrodeoxygenation catalyst is in a range of 5:1 to 8:1, preferably 5.5:1 to 7.5:1, and more preferably 5:1, 5.5:1, 6:1, 6.5:1, 7:1, 7.5:1, or 8:1. In some embodiments, the solvent includes a cycloalkane solvent, and preferably includes at least one of cyclohexane, n-hexane, and decalin.

In some embodiments, the hydrodeoxygenation is conducted at a temperature of 160° C. to 200° C., preferably 170° C. to 180° C., and more preferably 160° C., 165° C., 170° C., 175° C., 180° C., 185° C., 190° C., 195° C., or 200° C. In some embodiments, the hydrodeoxygenation is conducted for 1 h to 12 h, preferably 2 h to 11 h, and more preferably 1 h, 2 h, 3 h, 4 h, 5 h, 6 h, 7 h, 8 h, 9 h, 10 h, 11 h, or 12 h. In some embodiments, the hydrodeoxygenation is conducted at a hydrogen pressure of 0.5 MPa to 6 MPa, preferably 1 MPa to 5.5 MPa, and more preferably 0.5 MPa, 1 MPa, 1.5 MPa, 2 MPa, 2.5 MPa, 3 MPa, 3.5 MPa, 4 MPa, 4.5 MPa, 5 MPa, 5.5 MPa, or 6 MPa. During the hydrodeoxygenation, carbonyl bonds in the precursor compound of the tetracyclic hydrocarbon are broken, and small molecules of water are removed to obtain the tetracyclic hydrocarbon with a structure shown in formula II.

In some embodiments, after the hydrodeoxygenation, a post-treatment is conducted. In some embodiments, the post-treatment includes: subjecting a resulting reaction solution to a solid-liquid separation, concentrating an obtained liquid component and then purifying an obtained concentrated solution by vacuum distillation to obtain the tetracyclic hydrocarbon. There is no special limitation on the solid-liquid separation, and any solid-liquid separation methods well known to those skilled in the art may be used, such as filtration. There is no special limitation on the concentration, and any concentration method well known to those skilled in the art may be used, such as rotary evaporation. In some embodiments, the concentration is conducted at a temperature of 60° C. to 80° C., and preferably 70° C. to 80° C. The purpose of the concentration is to remove lower-boiling solvents. In some embodiments, the purification is conducted by vacuum distillation. In some embodiments, the vacuum distillation is conducted at a pressure of 0.04 MPa to 0.1 MPa, and preferably 0.06 MPa to 0.08 MPa. In some embodiments, the vacuum distillation is conducted at a temperature of 150° C. to 220° C., and preferably 180° C. to 200° C. In the present disclosure, the tetracyclic hydrocarbon with a high boiling point could be obtained by purification through vacuum distillation.

The present disclosure further provides use of the tetracyclic hydrocarbon or the tetracyclic hydrocarbon prepared by the method described above as a fuel. In some embodiments, the fuel includes an aerospace fuel, and preferably an aircraft fuel. In some embodiments, the aircraft includes an aircraft or a missile. In the present disclosure, the tetracyclic hydrocarbon exhibits a high density, a high volumetric net calorific value, and a low freezing point and excellent combustion and low-temperature resistance properties. When being used as a fuel, the tetracyclic hydrocarbon could exhibit dual functions of ensuring the flexibility and portability of an aircraft and effectively improving the range, speed, payload and other aircraft performances of the aircraft. Therefore, the tetracyclic hydrocarbon has desirable application prospects in the aerospace field.

The technical solutions of the present disclosure will be clearly and completely described below with reference to the examples of the present disclosure. Apparently, the described examples are merely a part rather than all of the examples of the present disclosure. All other embodiments obtained by those skilled in the art based on the embodiments of the present disclosure without creative efforts shall fall within the scope of the present disclosure.

Example 1

(1) In a 50 mL single-port quartz glass reactor, 59 mmol norbornene, 59 mmol cyclohexenone, and 10 mL methanol were added to obtain a mixture. Then, nitrogen was continuously bubbled into the mixture for 60 min under stirring at ambient temperature. Then, the mixture was sealed in a condenser tube, and condensed water was turned on to control a reaction temperature to 20° C. The mixture was reacted under irradiation of 365 nm LED light for 9 h. After the reaction, a resulting reaction product was subjected to rotary-evaporated at 50° C., and then a resulting rotary-evaporated product was purified by vacuum distillation at 0.08 MPa and 180° C. to obtain a crude precursor compound of a tetracyclic hydrocarbon.

The crude precursor compound of the tetracyclic hydrocarbon was qualitatively analyzed by using gas chromatography-mass spectrometry. FIG. 1 shows a mass spectrum of the precursor compound of the tetracyclic hydrocarbon. From FIG. 1, it can be seen that, the precursor compound of the tetracyclic hydrocarbon has a maximum molecular weight of 190 and characteristic fragment peaks of 97, 162, and 175, indicating that the precursor compound of the tetracyclic hydrocarbon with the structure shown in formula I is prepared in the present disclosure.

A gas chromatograph equipped with an FID detector and an HP-5 capillary column was used to quantitatively calculate the conversion rate of the reactant norbornene and the selectivity and yield of the precursor compound of the target product tetracyclic hydrocarbon, as shown in Table 1.

(2) 10 g of the crude precursor compound of the tetracyclic hydrocarbon was added into a 100 mL autoclave with mechanical stirring, 0.025 g of Pd/C catalyst, 0.2 g of H-Y molecular sieve, and 50 mL of cyclohexane were added thereto to obtain a mixed material. Gas in the autoclave was replaced with nitrogen 3 times and hydrogen 3 times in sequence. The mixed material was subjected to reaction under a hydrogen pressure of 6 MPa at 180° C. for 12 h. Then, a resulting reaction product was filtered, and a resulting liquid component was rotary-evaporated at 70° C., and then a resulting rotary-evaporated product was subjected to vacuum distillation at 0.08 MPa and 180° C. to obtain the tetracyclic hydrocarbon. The tetracyclic hydrocarbon is analyzed by gas chromatography-mass spectrometry and a nuclear magnetic resonance spectrometer to determine the structure and purity of the tetracyclic hydrocarbon, as shown in Table 2.

Figure 2:
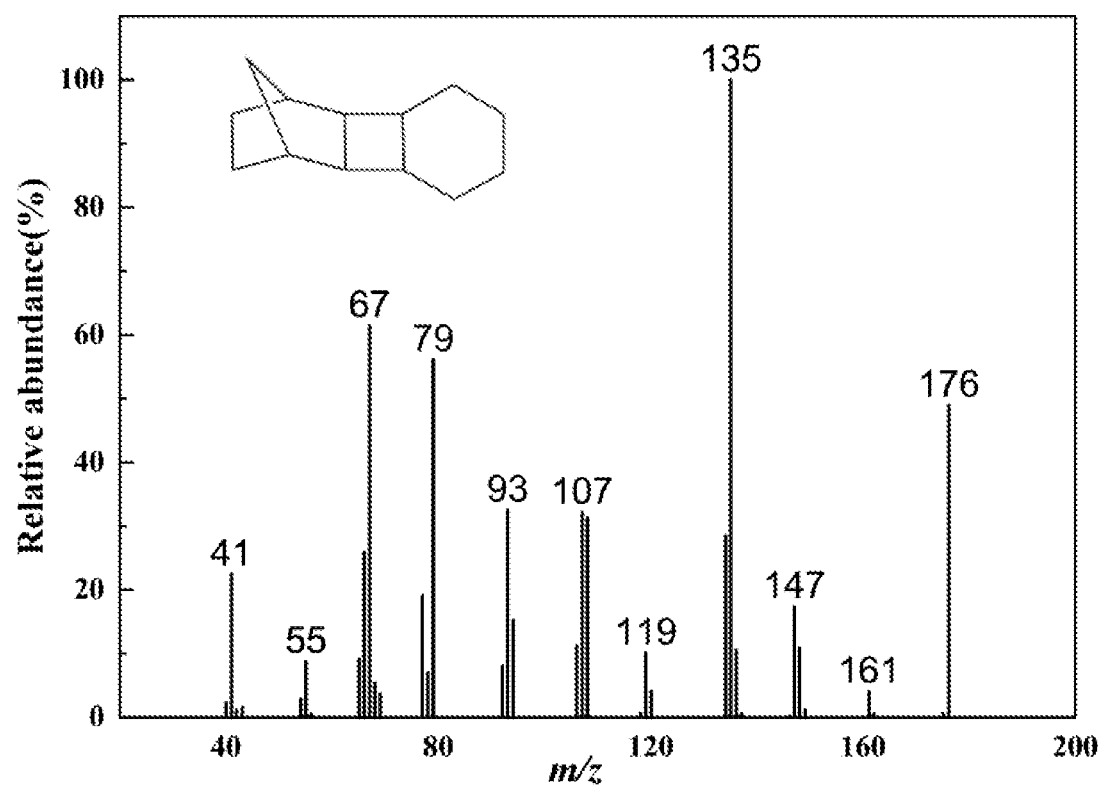
FIG. 2 shows a mass spectrum of the tetracyclic hydrocarbon prepared in Example 1.

FIG. 2 shows a mass spectrum of the tetracyclic hydrocarbon. From FIG. 2, it can be seen that the tetracyclic hydrocarbon compound has a maximum molecular mass of 176, and has characteristic fragment peaks such as 93, 107, and 135, indicating that the tetracyclic hydrocarbon with a structure shown in formula II is prepared in the present disclosure.

The density and volumetric net calorific value of the tetracyclic hydrocarbon prepared in Example 1 and the fuels JP-10, RJ-4, and RJ-4-I are shown in Table 1. The density was tested by GB/T 1884-2000, the volumetric net calorific value was tested by GB/T 384-1981, and the freezing point was tested by GB/T 2430-2008.

TABLE 1

| Fuel performance test results | | | |
|---|---|---|---|
| Fuel | Density (g/cm$^3$) | Volumetric net calorific value (MJ/L) | Freezing point (° C.) |
| JP-10 | 0.936 | 39.4 | |
| RJ-4 | 0.927 | 39.0 | |
| RJ-4-I | 0.911-0.918 | 38.5 | |
| Tetracyclic hydrocarbon | 0.986 | 41.14 | <−60 |

As shown in Table 1, the tetracyclic hydrocarbon prepared by the present disclosure has high density, high volumetric net calorific value, and low freezing point, which show better overall performances than fuels JP-10, RJ-4, and RJ-4-I. From this, it can be indicated that the tetracyclic hydrocarbon prepared by the present disclosure has a high density, a high calorific value, a low freezing point, and excellent combustion and low-temperature resistance properties, which could effectively improve the range, speed, and load of the aircraft.

Examples 2 to 18

Examples 2-18 were performed to prepare precursor compounds of the tetracyclic hydrocarbons according to the method in Example 1, where the preparation conditions were shown in Table 2. The preparation conditions not listed in Table 2 were the same as those in Example 1.

TABLE 2

| Preparation conditions and reaction results of the precursor compounds of the tetracyclic hydrocarbons in Examples 1 to 18 | | | | | | | | | |
|---|---|---|---|---|---|---|---|---|---|
| Examples | Norbornene/ mmol Cyclohexenone/ mmol | Organic solvent | Light flux mW/cm$^2$ | Molar ratio of norbornene cyclohexenone | Reaction temperature (° C.) | Reaction time/h | Norbornene conversion rate/% | Target product selectivity/% | Target product yield/% |
| Example 1 | 96 24 | Methanol | 100 | 4:1 | 20 | 9 | 64.45 | 21.63 | 13.94 |
| Example 2 | 90 30 | Methanol | 100 | 3:1 | 20 | 9 | 63.65 | 26.55 | 16.90 |

TABLE 2-continued

Preparation conditions and reaction results of the precursor compounds of the tetracyclic hydrocarbons in Examples 1 to 18

| Examples | Norbornene/ mmol Cyclohexenone/ mmol | Organic solvent | Light flux mW/cm$^2$ | Molar ratio of norbornene cyclohexenone | Reaction temperature (° C.) | Reaction time/h | Norbornene conversion rate/% | Target product selectivity/% | Target product yield/% |
|---|---|---|---|---|---|---|---|---|---|
| Example 3 | 80 40 | Methanol | 100 | 2:1 | 20 | 9 | 58.24 | 37.56 | 21.87 |
| Example 4 | 59 59 | Methanol | 100 | 1:1 | 20 | 9 | 46.43 | 55.67 | 25.85 |
| Example 5 | 59 59 | Methanol | 100 | 1:1 | 20 | 6 | 35.76 | 54.56 | 19.51 |
| Example 6 | 59 59 | Methanol | 100 | 1:1 | 20 | 3 | 17.86 | 52.26 | 9.33 |
| Example 7 | 40 80 | Methanol | 100 | 1:2 | 20 | 9 | 38.21 | 76.25 | 19.14 |
| Example 8 | 30 90 | Methanol | 100 | 1:3 | 20 | 9 | 29.25 | 82.36 | 24.09 |
| Example 9 | 24 96 | Methanol | 100 | 1:4 | 20 | 9 | 18.98 | 88.82 | 16.86 |
| Example 10 | 59 59 | Methanol | 50 | 1:1 | 20 | 9 | 26.28 | 34.91 | 9.17 |
| Example 11 | 59 59 | Methanol | 150 | 1:1 | 20 | 9 | 57.26 | 61.35 | 35.13 |
| Example 12 | 59 59 | Ethanol | 100 | 1:1 | 20 | 9 | 45.63 | 54.62 | 24.92 |
| Example 13 | 59 59 | Dichloromethane | 100 | 1:1 | 20 | 9 | 36.55 | 48.97 | 17.90 |
| Example 14 | 59 59 | Cyclohexane | 100 | 1:1 | 20 | 9 | 26.32 | 37.25 | 9.80 |
| Example 15 | 59 59 | Methanol | 100 | 1:1 | −10 | 9 | 45.89 | 54.78 | 25.14 |
| Example 16 | 59 59 | Methanol | 100 | 1:1 | 0 | 9 | 46.01 | 54.91 | 25.26 |
| Example 17 | 59 59 | Methanol | 100 | 1:1 | 10 | 9 | 46.20 | 55.21 | 25.51 |
| Example 18 | 59 59 | Methanol | 100 | 1:1 | 30 | 9 | 46.95 | 55.75 | 26.17 |

As shown in Table 2, the method for preparing the precursor compound provided by the present disclosure has a high conversion rate of raw materials, a high yield, and a high selectivity of the target product.

The above descriptions are merely preferred embodiments of the present disclosure. It should be noted that those skill in the art may further make several improvements and modifications without departing from the principle of the present disclosure, but such improvements and modifications should be deemed as falling within the scope of the present disclosure.

What is claimed is:

1. A tetracyclic hydrocarbon, having a structure shown in formula II:

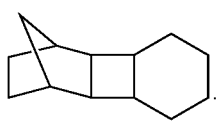

formula II

2. A method for preparing the tetracyclic hydrocarbon of claim 1, comprising the following steps:
    subjecting a precursor compound of the tetracyclic hydrocarbon to hydrodeoxygenation in a hydrogen atmosphere to obtain the tetracyclic hydrocarbon;
    wherein the precursor compound of the tetracyclic hydrocarbon has a structure shown in formula I:

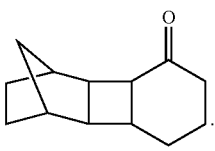

formula I

3. The method of claim 2, wherein the hydrodeoxygenation is conducted in the presence of a hydrodeoxygenation catalyst, a molecular sieve, and a solvent;
    the hydrodeoxygenation catalyst is selected from a transition metal catalyst;
    the molecular sieve is at least one selected from the group consisting of an H-Y molecular sieve, a Pt/H-Y molecular sieve, a ZSM-5 molecular sieve, and an H-β molecular sieve;
    a mass ratio of the molecular sieve to the hydrodeoxygenation catalyst is in a range of 5:1 to 8:1;
    the solvent is selected from a cycloalkane solvent; and
    the hydrodeoxygenation is conducted at a temperature of 160° C. to 200° C. and a hydrogen pressure of 0.5 MPa to 6 MPa for 1 h to 12 h.

4. The method of claim 2, wherein the precursor compound of the tetracyclic hydrocarbon is prepared by a process comprising the following steps: subjecting norbornene and cyclohexenone to photosensitized cycloaddition under ultraviolet (UV) irradiation to obtain the precursor compound of the tetracyclic hydrocarbon.

5. The method of claim 4, wherein a molar ratio of the norbornene to the cyclohexenone is in a range of 1:4 to 4:1.

6. The method of claim 4, wherein the photosensitized cycloaddition is conducted in an organic solvent, and the organic solvent comprises at least one selected from the group consisting of an alcohol solvent, a chlorinated alkane solvent, and a cycloalkane solvent.

7. The method of claim 4, wherein the photosensitized cycloaddition is conducted at a temperature of −10° C. to 30° C. for 1 h to 9 h; and the UV irradiation has an incident light flux of 50 mW/cm$^2$ to 150 mW/cm$^2$.

\* \* \* \* \*